US00PP14151P29

(12) United States Plant Patent
Cornelis

(10) Patent No.: US PP14,151 P2
(45) Date of Patent: Sep. 16, 2003

(54) SPATHIPHYLLUM PLANT NAMED 'CORSPABONT'

(76) Inventor: Daniel Cornelis, Oude Gaverweg 2, B-9820 Melsen-Merelbeke (BE)

( * ) Notice: Subject to any disclaimer, the term of this patent is extended or adjusted under 35 U.S.C. 154(b) by 0 days.

(21) Appl. No.: 10/230,138

(22) Filed: Aug. 29, 2002

(51) Int. Cl.[7] ..... A01H 5/00

(52) U.S. Cl. ..... Plt./364
(58) Field of Search ..... Plt./364

*Primary Examiner*—Bruce R. Campell
*Assistant Examiner*—Susan B. McCormick
(74) *Attorney, Agent, or Firm*—Foley & Lardner

(57) ABSTRACT

A new and distinct Spathiphyllum plant named 'Corspabont' characterized by having variegated leaves, white flowers fading to variegated, slow growth rate, and compact, small size.

2 Drawing Sheets

Latin name of the genus and species of the plant claimed: Spathiphyllum (species unknown).
Variety denomination: 'Corspabont'.

BACKGROUND OF THE INVENTION

The present invention relates to a new and distinct cultivar of Spathiphyllum plant, hereinafter referred to by the cultivar name 'Corspabont'.

The new cultivar originated from a cross made in a controlled breeding program in Melsen-Merelbeke, Belgium, in the year 2000. The female parent is 'Domino' (U.S. Plant Pat. No. 9,944). The male parent is 'Alpha CD' (U.S. Plant Pat. No. 10,823). 'Corspabont' was discovered and selected by the inventor, Daniel Cornelis, as a flowering plant within the progeny of the stated cross in a controlled environment in Melsen-Merelbeke, Belgium.

Asexual reproduction of the new cultivar was first performed by tissue culture in October 2001 in Hamme, Belgium and has demonstrated that the combination of characteristics as herein disclosed for the new cultivar are firmly fixed and retained through successive generations of asexual reproduction true to type.

BRIEF DESCRIPTION OF THE INVENTION

The following traits have been repeatedly observed and are determined to be basic characteristics of 'Corspabont' which in combination distinguish this Spathiphyllum as a new and distinct cultivar:

1. variegated leaves;
2. slow growth rate;
3. white flowers fading to variegated; and
4. compact, small size.

'Corspabont' has not been observed under all possible environmental conditions. The phenotype of the new cultivar may vary significantly with variations in environment such as temperature, light intensity, and day length without any change in the genotype of the plant.

Of the many commercial cultivars known to the present inventor, the most similar in comparison to 'Corspabont' is the parental cultivar 'Domino'. 'Corspabont' has significantly less green coloration in its leaves whereas the leaves of 'Domino' are predominantly green with some white. The male parent 'Alpha CD' has dark green leaves without any variegation. The growth rate of 'Corspabont' is about twice as slow as the growth rate of 'Domino'. 'Corspabont' is smaller and more compact than 'Domino' and therefore more suitable for cultivation in smaller container sizes.

BRIEF DESCRIPTION OF THE DRAWING

The accompanying photographic drawings show a 24-month old 'Corspabont' plant. On the lower left is a close-up of a 'Corspabont' flower. On lower right is a comparison close-up of the leaves of 'Corspabont' and 'Domino'.

DETAILED BOTANICAL DESCRIPTION

The following observations, measurements and values describe the new cultivar at 24 months grown in Melsem-Merelbeke, Belgium under conditions which closely approximate those generally used in commercial practice. Grown in standard glasshouses in well-drained peat. Ideal growing conditions under which this plant is grown is 21–23 degrees Celsius during the day and 20 degrees Celsius at night. Gibberalic acid is added for flower initiation (amount depends on the pot size, plant development and age of plant). The described plant was asexually reproduced by tissue culture.

Color references are made to The Royal Horticultural Society Colour Chart (R.H.S.), except where general colors of ordinary significance are used. Color values were taken under daylight conditions at approximately 3:00 p.m. in Boskoop, The Netherlands.

Plant:

*Appearance.*—Broad upright with leaf petioles growing directly from base.
*Height.*—Average 60 cm.
*Width.*—Average 60 cm.
*Growth habit.*—Moderately vigorous.
*Winter hardiness.*—USDA Zone 10.
*Stems.*—Leaves grow directly from base, so no stems are visible.
*Time to initiate roots.*—3 to 4 weeks under average temperature of 21° Celsius.
*Time to develop roots.*—5 to 6 weeks under average temperature of 21° Celsius.
*Rooting habit.*—Freely branching.

Foliage:

*Shape.*—Narrow ovate to lanceolate.

*Apex.*—Acute.

*Base.*—Attenuate.

*Texture.*—Smooth, somewhat sinuate (due to variegation) only slightly glossy, somewhat leathery.

*Leaf color.*—Green, closest to but darker than RHS 139A, heavily marbled white RHS 155 C to greyed-yellow RHS 160C with some greyed-green areas RHS 189A; young leaves are green closest to but darker than RHS 141, heavily marbled yellow green between RHS 145C and RHS 145D to 149D (both upper and lower surfaces).

*Midrib color.*—Upper Surface: Green RHS 139A, striped green-white RHS 157D. Lower Surface: Green between RHS 143B and RHS 143C.

*Leaf size.*—Width: Average 7.6 cm. Length: Average 22.5 cm (excluding petiole).

*Petiole.*—Average length 16.4 cm, average diameter 4.5 mm, petiole somewhat flattened, green RHS 141A.

*Petiole sheath.*—Average 14.6 cm long and 8 mm wide (measured at halfway point), color green RHS 139A with lighter stripes between RHS 141A and RHS 141B.

*Geniculum.*—Average length 3 cm, average width 6 mm, green RHS 143B.

*Veins.*—Average 13 pairs of furrowed secondary veins, upper side color not distinctively differing from the upper side leaf color: green, closest to but darker than RHS 139A, with white RHS 155 C to greyed-yellow; RHS 160C with some greyed-green parts RHS 189A, under side green RHS 143C to yellow-green RHS 144B.

Inflorescence description:

*Immature.*—Peduncle: Average length 17.5 (measured from top of petiole sheath to base spathe), average diameter 4 mm, rounded, green in color, between RHS 143A and RHS 143B. Spathe: Average length 9 cm, average width 4.2 cm, cupped, average depth 1 cm.

*Mature.*—Spathe: Size: Average length 9.5 cm, average width 4.5 cm, cupped, average depth 1.2 cm. Color: Unopened Bud: Yellow-green between RHS 145C and RHS 145D; marbled yellow-green between RHS 144A and RHS 144B. Fully Open: Front surface: Green-white between RHS 157C and 157D to white RHS 155C, marbled yellow-green between RHS 144C and 144D. Back Surface: Green-white RHS 157C to 157D to white RHS 155C, marbled yellow-green between RHS 144C and 144D. Apex: Apiculate, green RHS 143C. Faded: Front Surface: Yellow-green between RHS 144C and 144D, marbled green RHS 141A (or slightly darker). Back Surface: Yellow-green between RHS 144C and 144D, marbled green RHS 141A (or slightly darker). Apex: Apiculate. Arrangement: Solitary. Shape: Ovate. Margins: Entire. Fragrance: Sweet, very faint. Lastingness of the individual inflorescence: Average: four weeks (including time that flowers has become variegated).

Reproductive organs:

*Spadix.*—Size: Average length 5.5 cm, average width 1.5 cm. Quantity: Average approximately 140 individual flowers per spadix. Color: Yellow-white between RHS 160C and RHS 160D (cream color). Stamens: 6, pressed against styles. Pistil: Each individual flower has one pistil with a triparted stigma; the pistil has an average length of 2 mm and is yellow-white in color RHS 158D.

*Pollen.*—Amount: Very low. Color: Yellow-white between RHS 158A and RHS 158B.

*Seed production.*—None observed to date.

*Fruit production.*—None observed to date.

Disease resistance/susceptibility: No known diseases typical to Spathiphyllum plants observed to date on plants grown under commercial greenhouse conditions.

I claim:

1. A new and distinct Spathiphyllum plant named 'Corspabont', substantially as illustrated and described herein.

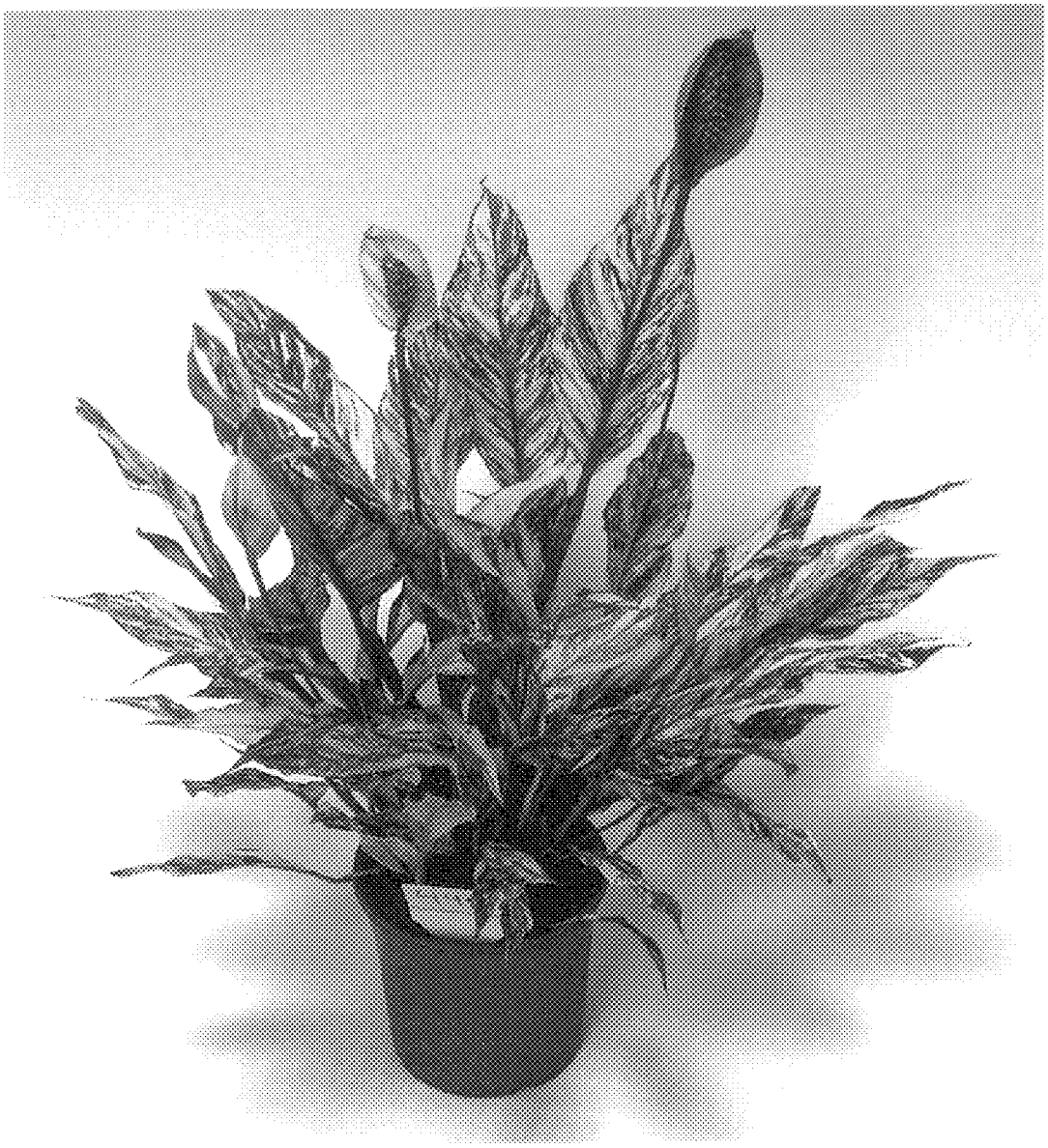
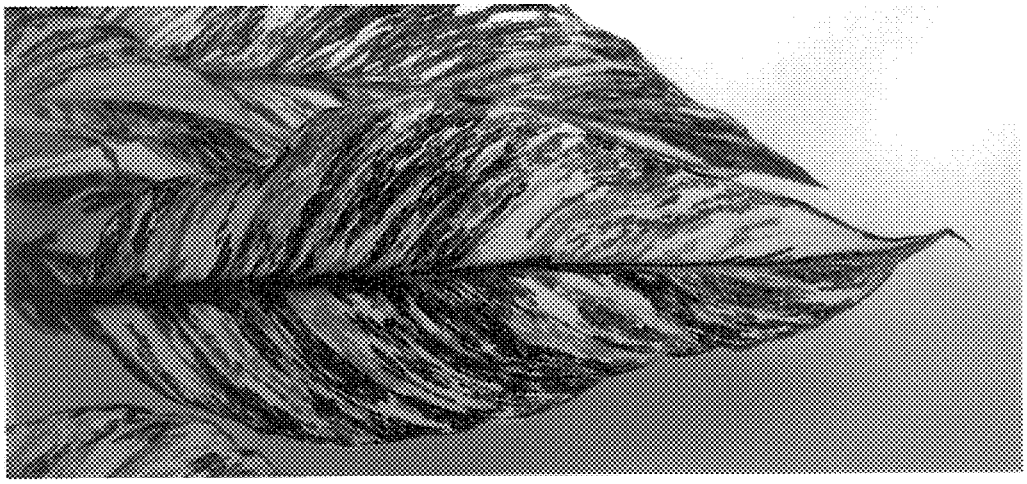

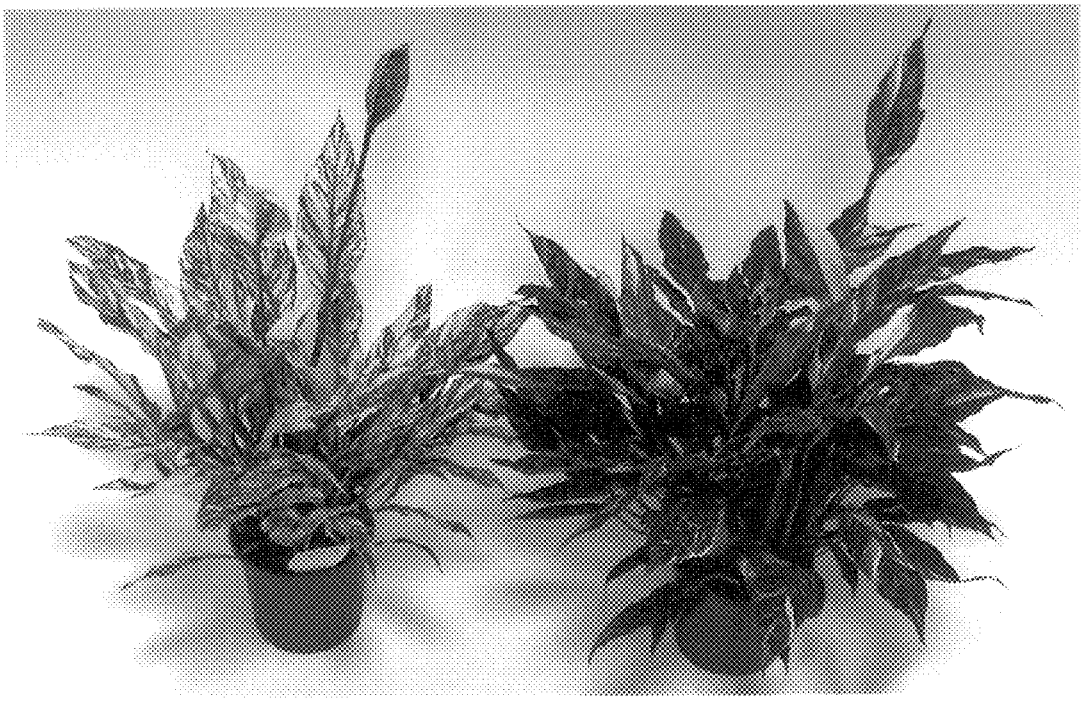
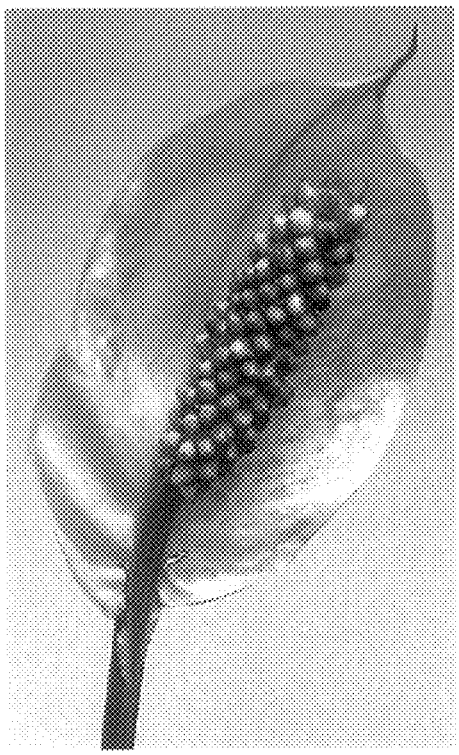
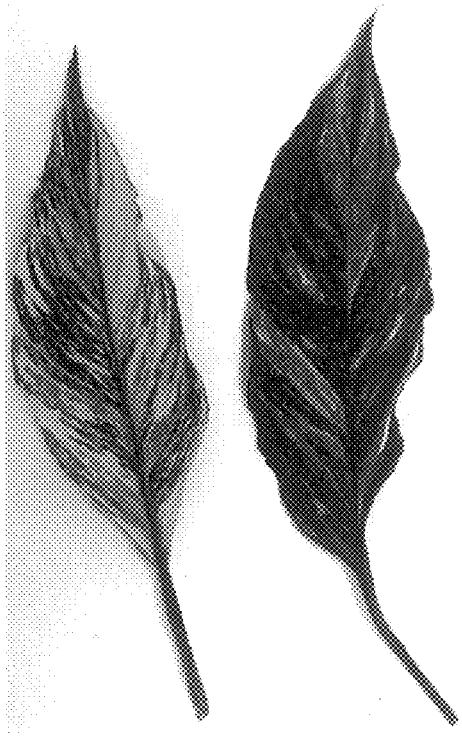

* * * * *